United States Patent
Wan et al.

(10) Patent No.: US 7,166,639 B2
(45) Date of Patent: Jan. 23, 2007

(54) NF-κB INHIBITORS

(75) Inventors: Zehong Wan, King of Prussia, PA (US); Joelle L. Burgess, Collegeville, PA (US); James F. Callahan, King of Prussia, PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 462 days.

(21) Appl. No.: 10/491,710

(22) PCT Filed: Oct. 4, 2002

(86) PCT No.: PCT/US02/31902

§ 371 (c)(1),
(2), (4) Date: Apr. 2, 2004

(87) PCT Pub. No.: WO03/029242

PCT Pub. Date: Apr. 10, 2003

(65) Prior Publication Data

US 2004/0192943 A1 Sep. 30, 2004

Related U.S. Application Data

(60) Provisional application No. 60/326,976, filed on Oct. 4, 2001.

(51) Int. Cl.
*A61K 31/38* (2006.01)
*C07D 333/36* (2006.01)

(52) U.S. Cl. .................................... 514/447; 549/68

(58) Field of Classification Search ............... 514/447; 549/68

See application file for complete search history.

(56) References Cited

U.S. PATENT DOCUMENTS

| | | | |
|---|---|---|---|
| 3,963,750 A | 6/1976 | Goudie | 260/332.2 |
| 5,422,335 A | 6/1995 | Hagen et al. | |
| 6,143,777 A | 11/2000 | Jonas et al. | |
| 6,274,590 B1 * | 8/2001 | Talley et al. | 514/277 |
| 6,414,013 B1 * | 7/2002 | Fancelli et al. | 514/438 |
| 6,835,745 B1 * | 12/2004 | Coghlan et al. | 514/448 |
| 6,881,735 B1 * | 4/2005 | Schindler et al. | 514/227.8 |
| 6,881,741 B1 * | 4/2005 | Chan Chun Kong et al. | 514/91 |
| 7,019,027 B1 * | 3/2006 | Linden et al. | 514/447 |
| 7,084,178 B1 * | 8/2006 | Marcin et al. | 514/604 |
| 7,098,240 B1 * | 8/2006 | Griffiths et al. | 514/447 |

FOREIGN PATENT DOCUMENTS

| WO | WO 01/58890 | 8/2001 |
|---|---|---|
| WO | WO 02/30353 | 4/2002 |

* cited by examiner

*Primary Examiner*—Deborah C. Lambkin
(74) *Attorney, Agent, or Firm*—John L. Lemanowicz; James C. Kellerman; Laura K. Madden

(57) ABSTRACT

The present invention provides novel compounds and methods for using them to treat diseases with aminothiophene inhibitors of IKK-β phosphorylation of IκB. In so doing these aminothiophene inhibitors block pathological activation of transcription factor NF-κB in which diseases excessive activation of NF-κB is implicated.

17 Claims, No Drawings

NF-κB INHIBITORS

CROSS REFERENCES TO RELATED APPLICATIONS

This application is a National Stage Application filed under 35 U.S.C.§ 371 of PCT/US02/31902, filed on Oct. 4, 2002, which claims priority of U.S. Provisional Application No. 60/326,976, filed Oct. 4, 2001.

FIELD OF THE INVENTION

This invention relates in general to a method of inhibiting pathological activation of the transcription factor NF-κB (nuclear factor-κB) using aminothiophene compounds. Such methods are particularly useful for treating diseases in which activation of NF-κB is implicated. More specifically, these methods may be used for inhibiting IKK-β (IκB kinase-β) phosphorylation of IκB (inhibitory protein κB)-which prevents subsequent degradation and activation of NF-κB dimers. Such methods are useful in the treatment of a variety of diseases associated with NF-κB activation including inflammatory and tissue repair disorders; particularly rheumatoid arthritis, inflammatory bowel disease, asthma and COPD (chronic obstructive pulmonary disease) osteoarthritis; osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, Ataxia Telangiestasia.

BACKGROUND OF THE INVENTION

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors. Recent breakthroughs in the elucidation of regulatory mechanisms involved in the transcription and translation of a variety of mediators have led to increased interest in therapeutic approaches directed at the level of gene transcription.

Nuclear factor κB (NF-κB) belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκB is phosphorylated on two N-terminal serines by the recently identified IκB kinases (IKK-α and IKK-β). Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immunoregualtory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.*, 271, 31496–31501 (1996). Expression of IKK-β has been shown in synoviocytes of rheumatoid arthritis patients and gene transfer studies have demonstrated the central role of IKK-β in stimulated inflammatory mediator production in these cells. See Aupperele et al. *J. Immunology* 1999. 163:427–433 and Aupperle et al. *J. Immunology* 2001; 166:2705–11. More recently, the intra-articular administration of a wild type IKK-β adenoviral construct was shown to cause paw swelling while intra-articular administration of dominant-negative IKK-β inhibited adjuvant-induced arthritis in rat. See Tak et al. *Artitritis and Rheumcatism* 2001; 44:1897–1907.

The NF-κB/Rel and IκB proteins are also likely to play a key role in neoplastic transformation and metastasis. Family members are associated with cell transformation in vitro and in vivo as a result of overexpression, gene amplification, gene rearrangements or translocations. In addition, rearrangement and/or amplification of the genes encoding these proteins are seen in 20–25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported, strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-κB activation may be useful chemotherapeutic agents as either single agents or adjunct therapy. Recent reports have implicated NF-κB as an inhibitor of skeletal cell differentiation as well as a regulator of cytokine-induced muscle wasting (Gutridge et al. *Science;* 2000; 289:2363–2365.) further supporting the potential of NF-κB inhibitors as novel cancer therapies.

Several NF-κB inhibitors are described in C. Wahl, et al. *J. Clin. Invest.* 101(5), 1163–1174 (1998), R. W. Sullivan, et al. *J. Med. Chem.* 41, 413–419 (1998), J. W. Pierce, et al. *J. Biol. Chem.* 272, 21096–21103 (1997)

The marine natural product hymenialdisine is known to inhibit NF-κB. Roshak, A., et al., *JPET,* 283, 955–961 (1997). Breton, J. J and Chabot-Fletcher, M. C., *JPET,* 282, 459–466 (1997).

Additionally, patent applications have been filed on indole and benzimidazole inhibitors of the IKK complex, see DE 19928424 and WO200130774, and the natural products staurosporine, quercetin, K252a and K252b have been shown to be IKK-β inhibitors, see Peet, G. W. and Li, J. J. *Biol. Chem.,* 274, 32655–32661 (1999) and Wisniewski, D., et al., *Analytical Biochem.* 274, 220–228 (1999).

U.S. Pat. No. 3,963,750 describes the preparation of certain aminothiophenes.

SUMMARY OF THE INVENTION

The present invention involves novel compounds and novel methods of inhibiting the activation transcription factor NF-κB using the present compounds.

An object of the present invention is to provide a method for treating diseases which may be therapeutically modified by altering the activity of transcription factor NF-κB.

Accordingly, in the first aspect, this invention provides a pharmaceutical composition comprising a compound according to Formula I.

In another aspect, this invention provides a method of treating diseases in which the disease pathology may be therapeutically modified by inhibiting phosphorylation and subsequent degradation of IκB by IKK-β.

In still another aspect, this invention provides a method of treating diseases in which the disease pathology may be therapeutically modified by inhibiting pathological activation of NF-κB.

In a particular aspect, this invention provides methods for treating a variety of diseases associated with NF-κB activation including inflammatory and tissue repair disorders, particularly rheumatoid artritis, inflammatory bowel disease, asthma and COPD (chronic obstructive pulmonary disease) osteoarthritis, osteoporosis and fibrotic diseases, dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome and Ataxia Telangiestasia

DETAILED DESCRIPTION OF THE INVENTION

The compounds of the present invention are selected from Formula (I) herein below:

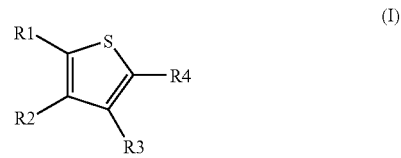

wherein:

$R_1$ is $CONH_2$, or $SO_2NH_2$;

$R_2$ is $NR_5R_6$ $R_3$ is H, or halogen;

$R_4$ is aryl or heteroaryl;

$R_5$ is H or alkyl;

provided that when $R_1$ is $CONH_2$, $R_6$ is selected from the group consisting of H, CO-alkyl, $SO_2$-alky, $CONH_2$, CONH-alkyl, CONH-aryl, CONH-heteroaryl, $CSNH_2$, CSNH-alkyl, CSNH-aryl, CSNH-heteroaryl, $SO_2NH_2$, $SO_2NH$-alkyl, $SO_2NH$-aryl, and $SO_2NH$-heteroaryl;

When $R_1$ is $SO_2NH_2$, $R_6$ is $CONH_2$; and when $R_1$ is $CONH_2$, $R_2$ is not $NHCONH_2$; and pharmaceutically acceptable salts, hydrates and solvated thereof.

Preferred compounds useful in the present invention include: 3-Acetylamino-5-(4-chloro-phenyl)-thiophene-2-carboxylic acid amide; 3-Acetylamino-5-(4-fluoro-phenyl)-thiophene-2-carboxylic acid amide; 5-(4-Fluoro-phenyl)-3-ureido-thiophene-2-sulfonic acid amide; 5-(3-Chloro-phenyl)-3-ureido-thiophene-2-sulfonic acid amide; 5-(4-Trifluoromethyl-phenyl)-3-ureido-thiophene-2-sulfonic acid amide; and 5-phenyl-3-ureido-thiophene-2-sulfonic acid amide.

This invention provides methods for treating a variety of diseases associated with NF-κB activation including inflammatory and tissue repair disorders; particularly rheumatoid arthritis, inflammatory bowel disease, asthma and COPD (chronic obstructive pulmonary disease) osteoarthritis, osteoporosis and fibrotic diseases; dermatosis, including psoriasis, atopic dermatitis and ultraviolet radiation (UV)-induced skin damage; autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including aquired immune deficiency syndrome (AIDS), adult respiratory distress syndrome, and Ataxia Telangiestasia.

Definitions

The present invention includes all hydrates, solvates, complexes and prodrugs of the compounds of this invention. Prodrugs are any covalently bonded compounds, which release the active parent, drug according to Formulas I and II in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form. and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I or any subformula thereof is independent of its meaning, or any other substituent's meaning, at any other occurrence, unless specified otherwise.

As used herein, "alkyl" refers to an optionally substituted hydrocarbon group joined by single carbon-carbon bonds and having 1–6 carbon atoms joined together. The alkyl hydrocarbon group may be linear, branched or cyclic, saturated or unsaturated. Substituents on optionally substituted alkyl are selected from the group consisting of aryl, OH, O-alkyl, CO, halogen, $CF_3$, and $OCF_3$.

As used herein, "aryl" refers to an optionally substituted aromatic group with at least one ring having a conjugated pi-electron system, containing up to two conjugated or fused ring systems. Aryl includes carbocyclic aryl, and biaryl groups, all of which may be optionally substituted. Substituents are selected from the group consisting of halogen, $C_{1-4}$ alkyl, $NH_2$, $OCF_3$, $CF_3$, O-alkyl, S-alkyl, CN, CHO, $SO_2$-alkyl and $N_2$.

As used herein, "heteroaryl" refers to an optionally substituted aromatic group with at least one ring having a conjugated pi-electron system, containing up to two conjugated or fused ring systems and 1–3 heteroatoms selected from O, S and N. Heteroaryl includes carbocyclic heteroarylaryl, aryl-heteroaryl and biheteroarylaryl groups, all of which may be optionally substituted. Preferred aryl include phenyl and naphthyl. More preferred aryl include phenyl. Preferred substituents are selected from the group consisting of halogen, $C_{1-4}$ alkyl, $NH_2$, $OCF_3$, $CF_3$, O-alkyl, S-alkyl, CN, CHO, $SO_2$-alkyl and $NO_2$. Examples of heteroaryl rings included pyrrole, furan, thiophene, indole, isoindole, benzofuran, isobenzofuran, benzothiphene, pyridine, quinoline, isoquinoline, quinolizine, pyrazole, imidazole, isoxazole, oxazole, isothiazole, thiazole, pyridazine, pyrimidine, and pyrazine.

As used herein "halogen" refers to include F, Cl, Br, and I.

Methods of Preparation

The general preparation of the aminothiophene carboxylic amide analogs is shown in Schemes I and II. The synthesis started with commercially available aminothiophene carboxylic ester 1. Protection of the amino group with di-tert-butyl dicarbonate [$(Boc)_2O$] and hydrolysis of the ester provided acid 3. The resultant acid was activated with 1,1'-carbonyldiimidazole, followed by reaction with ammonium hydroxide and treatment with trifluoroacetic acid (TFA) then furnished the aminothiophene carboxylic amide 5. Compound 5 was readily tranformed to acetamide 6, sulfomyl amide 7a and methyl urea 7b.

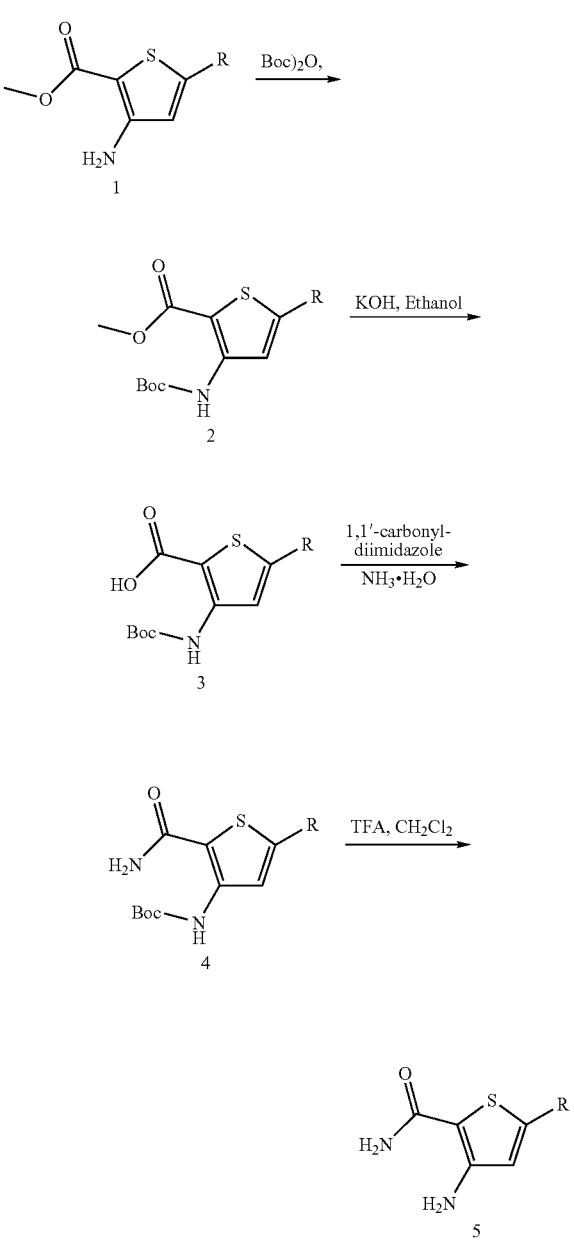

Scheme I

Scheme II

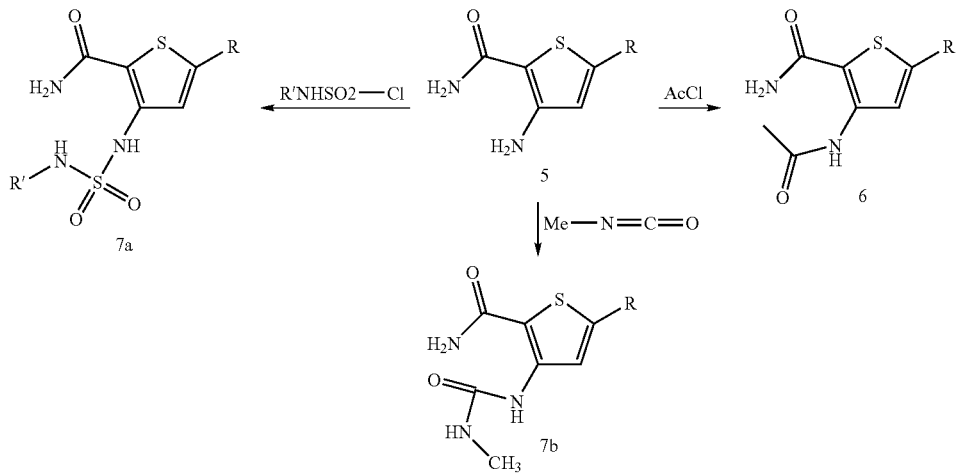

The general preparation of ureidothiophene sulfonamides is described in Scheme III. The synthesis started with tert-butyl sulfonamide 8. Deprotonation with n-BuLi followed by reaction with 4-methyl-benzenesulfonyl azide and sodium borohydride afforded amino-thiophene 9. Treatment with HCl and suzuki cross-coupling with 4-fluorophenyl-boronic acid provided amino-thiophene sulfonamide 11. The primary amine was then converted into urea 12.

Scheme III

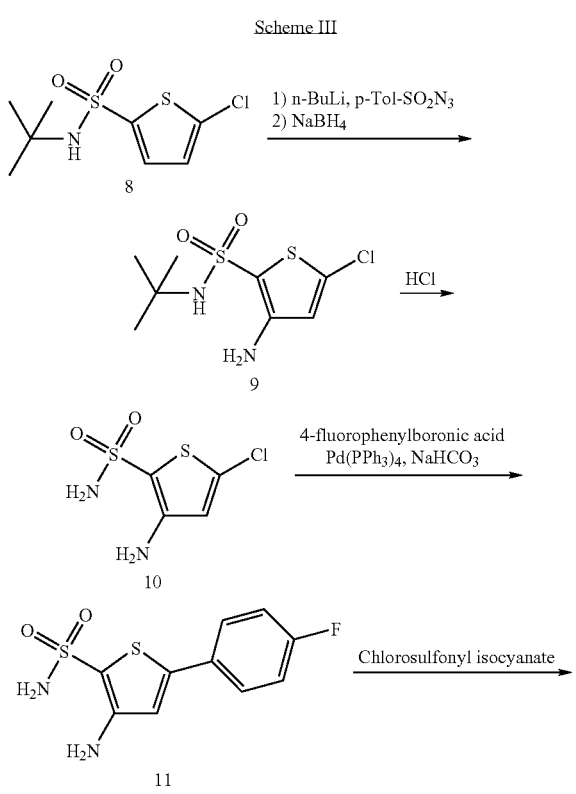

-continued

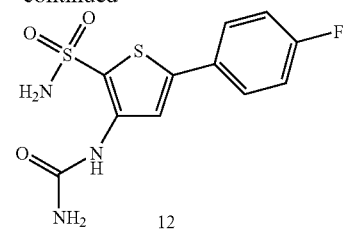

The following examples are intended to be illustrative of the present invention but not limiting in any way.

In general, nuclear magnetic resonance spectra were recorded at 400 MHz using Bruker AC 400 spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (d) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on MDS SCIEX (LC-MS) instrument using electrospray (ES) ionization technique. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel.

EXAMPLE 1

Preparation of 3-acetylanino-5-(4-chloro-phenyl)-thiophene-2-carboxylic acid amide 1a) 3-tert-Butoxycarbonylamino-5-(4-chloro-phenyl)-thiophene-2-carboxylic acid methyl ester To a solution of methyl 3-amino-5-(4-chlorophenyl)thiophene-2-carboxylate (1 g, 3.73 mmol) in THF (20 mL) was added 4-(dimethylamino)pyridine (45 mg, 0.373 mmol) and di-tert-butyl dicarbonate (1.22 g, 5.6 mmol). After stirring for 24 h at room temperature, the solution was diluted with brine solution (100 mL) and extracted with ethyl acetate (100 mL, 3×). The combined organic phases were dried over $MgSO_4$, filtered, and concentrated. Flash chromatography (hexanes/ethyl acetate, 4:1) then provided the title compound 1a as a white solid.

1b) 3-tert-Butoxycarbonylamino-5-(4-chloro-phenyl)-thiophene-2-carboxylic acid

A solution of 1a (1.37 g, 3.73 mmol) in ethanol (20 mL) was mixed with KOH (627 mg, 11.2 mmol) in water (20 mL). The resultant mixture was heated at 60° C. for 1 h, diluted with HCl (50 mL, 1N) and extracted with ethyl acetate (60 mL, 3×). The combined organic phases were dried over $MgSO_4$, filtered, and concentrated to afford compound 1b as a yellow solid.

1c) [2-Carbamoyl-5-(4-chloro-phenyl)-thiophene-3-yl]-carbamic acid tert butyl ester To a solution of 1b (1.3 g, 3.7 mmol) in DMF (10 mL) was added 1,1'-carbonyl diimidazole (1.2 g, 7.4 mmol). The resultant solution was stirred for 1 h and mixed with ammonium hydroxide (37%, 5 mL). The mixture was diluted with brine solution (100 mL) and extracted with ethyl acetate (100 mL). The combined organic phases were dried over $MgSO_4$, filtered, and concentrated. Flash chromatography (hexanes/ethyl acetate, 4:1) then provided compound 1c as a yellow solid.

1d) 3-Amino-5-(4-chloro-phenyl)-thiophene-2-carboxylic acid amide

To a solution of 1c (250 mg, 0.71 mmol) in $CH_2Cl_2$ (10 mL) was added TFA (1 mL). The resultant solution was stirred for 1 h, then mixed with saturated $NaHCO_3$ solution (60 mL), and extracted with ethyl acetate (50 mL, 3×). The combined organic phases were dried over $MgSO_4$, filtered, and concentrated. Flash chromatography (hexanes/ethyl acetate, 1:1) then provided compound 1d as a yellow solid: MS (ES) 253 $(M+H)^+$.

1e) 3-acetylamino-5-(4-chloro-phenyl)-thiophene-2-carboxylic acid amide A solution of 1d (20 mg, 0.079 mmol) in THF (10 mL) was treated with acetyl chloride (11.2 µL, 0.158 mmol) for 1 h. The resultant solution was diluted with water (0.1 mL) and DMSO (2 mL). The mixture was concentrated. Separation by reverse phase HPLC then provided the title compound as a white solid: MS (ES) 295 $(M+H)^+$; $^1H$ NMR (400 MHz, $CD_3SOCD_3$) δ11.08 (s, 1 H), 8.27 (s, 1 H), 7.69 (ws, 2 H), 7.68 (d, 2 H, J=8.8 Hz), 7.54 (d, 2 H, J=8.8 Hz), 2.14 (s, 3 H).

EXAMPLE 2

Preparation of 3-acetylamino-5-(4-fluoro-phenyl)-thiophene-2-carboxylic acid amide 2a) 3-amino-5-(4-fluoro-phenyl)-thiophene-2-carboxylic acid amide The compound was prepared from methyl 3-amino-5-(4-fluorophenyl)-thiophene-2-carboxylate by following the procedure in example 1a–1d. The compound is a yellow solid: MS (ES) 237 $(M+H)^+$.

2b) 3-acetylamino-5-(4-fluoro-phenyl)-thiophene-2-carboxylic acid amide

The title compound was prepared from 2a by following the procedure in example 1e. The compound is a white solid: MS (ES) 279 $(M+H)^+$; $^1H$ NMR (400 MHz, $CD_3SOCD_3$) δ11.09 (s, 1 H), 8.22 (s 1 H), 7.72–7.69 (m, 4 H), 7.35–7.30 (m, 2 H), 2.14 (s, 3 H).

EXAMPLE 3

Preparation of 5-(4-fluoro-phenyl)-3-ureido-thiophene-2-sulfonic acid amide 3a) 3-Amino-5-chloro-thiophene-2-sulfonic acid tert-butylamide To a solutuion of 5-chloro-thiophene-2-sulfonic acid tert-butylamide (310 mg, 1.22 mmol) in THF (10 mL) at −78° C. was added n-Buli (1.6 M in hexane, 1.7 mL, 2.7 mmol) dropwise. The resultant solution was warmed up to −30° C. and maintained at −20° C.--30° C. for 10 min. It was rmixed with a solution of 4-methylbenzenesulfonyl azide (361 mg, 1.83 mmol) in THF (2 mL). The mixture was stirred at ambient temperature for 1 h before diluted with brine solution (30 mL) and washed with toluene (20 mL). The organic phase was separated and mixed with $NaBH_4$ (500 mg, 13.2 mmol) and $H_2O$ (5 mL). The mixture was stirred for 2 h. at room temperature, then diluted with brine solution (50 mL) and washed with ethyl acetate (50 mL, 3×). The combined organic phases were dried over $MgSO_4$, filtered, and concentrated. Flash chromatography (hexanes/ethyl acetate, 4:1) then provided 3a (250 mg) as a yellow oil.

3b) 3-Amino-5-chloro-thiophene-2-sulfonic acid amide

A solution of 3a (250 mg, 0.93 mmol) in concentrated HCl solution (10 mL) was heated at 55° C. for 2h. Removal of all solvents then afforded 3b (198 mg) as a yellow solid.

3c) 3-Amino-5-(4-fluoro-phenyl)-thiophene-2-sulfonic acid amide

To a solution of 3b (104 mg, 0.5 mmol) in 1,4-dioxane/water (40 mL, 3:1) was added 4-fluorophenylboronic acid (140 mg, 1 mmol), $Na_2CO_3$ (212 mg, 2 mmol), and $Pd(PPh_3)_4$ (9% Pd, 59 mg, 0.05 mmoL). The resultant mixture was heated at 110° C. for 3 h, diluted with brine solution (50 mL) and extracted with ethyl acetate (50 mL, 3×). The combined organic phases were dried over $MgSO_4$, filtered, and concentrated. Flash chromatography (hexanes/ethyl acetate, 1:1) then provided 3c (45 mg, 33%) as a yellow solid: MS (ES) 273 $(M+H)^+$; $^1H$ NMR (400 MHz, MeOD) δ7.52 (m, 2 H), 7.04 (m, 2 H), 6.72 (s, 1 H).

3d) 5-(4-Fluoro-phenyl)-3-ureido-thiophene-2-sulfonic acid amide

To the mixture of 3c (30 mg, 0.11 mol) in $CH_2Cl_2$ (10 mL) was added chlorosulfonyl isocyanate (14 µL, 0.165 mmol). The resultant mixture was stirred at room temperature for 3 h, then mixed with water (0.5 mL). Separation using a reverse phase HPLC afforded 3d (20 mg, 58%) as a white solid: MS (ES) 316 $(M+H)^+$; $^1H$ NMR (400 MHz, $CD_3OD$) δ8.02 (s, 1 H), 7.69 (m, 2 H), 7.20 (m, 2 H).

EXAMPLE 4

Preparation of 5-(3-chloro-phenyl)-3-ureido-thiophene-2-sulfonic acid amide 4a) 3-Amino-5-(3-chloro-phenyl)-thiophene-2-sulfonic acid amide The title compound was prepared from 3-chlorobenzene boronic acide and 3b by following the procedure in example 3c. This compound is a white solid: MS (ES) 289 $(M+H)^+$; $^1H$ NMR (400 MHz, $CD_3OD$) δ7.62 (s 1 H), 7.53 (m, 1 H), 7.40 (m, 2 H), 6.92 (s, 1 H).

4b) 5-(3-Chloro-phenyl)-3-ureido-thiophene-2-sulfonic acid amide

The title compound was prepared from 4a by following the procedure in example 3d. This compound is a white solid: MS (ES) 332 (M+H)$^+$; $^1$H NMR (400 MHz, CD$_3$SOCD$_3$)δ8.28 (s, 1 H), 8.14 (s, 1 H), 7.72 (s, 2 H), 7.69 (s, 1 H), 7.60 (m, 1 H), 7.49 (m, 2 H), 6.72 (s, 2 H).

EXAMPLE 5

Preparation of 5-(4-trifluoromethyl-phenyl)-3-ureido-thiophene-2-sulfonic acid amide 5a) 3-Amino-5-(4-trifluoromethyl-phenyl)-thiophene-2-sulfonic acid amide The title compound was prepared from 4-trifluoromethylbenzene boronic acide and 3b by following the procedure in example 3c. This compound is a white solid: MS (ES) 323 (M+H)$^+$; $^1$H NMR (400 MHz, CD$_3$OD)δ7.80 (d, 2 H, J=8.2 Hz), 7.72 (d, 2 H, J=8.2 Hz), 7.02 (s, 1 H).

5b) 5-(4-trifluoromethyl-phenyl)-3-ureido-thiophene-2-sulfonic acid amide

The title compound was prepared from 5a by following the procedure in example 3d. This compound is a white solid: MS (ES) 366 (M+H)$^+$; $^1$H NMR (400 MHz, CD$_3$OD) δ8.20 (s, 1 H), 7.85 (d, 2 H, J=8.2 Hz), 7.75 (d, 2 H, J=8.2 Hz).

EXAMPLE 6

Preparation of 5-phenyl-3-ureido-thiophene-2-suffonic acid amide 6a) 3-Amino-5-phenyl-thiophene-2-sulfonic acid amide The title compound was prepared from phenylboronic acid and 3b by following the procedure in example 3c. This compound is a white solid: MS (ES) 255 (M+H)$^+$; $^1$H NMR (400 MHz, CD$_3$OD)δ7.61 (m, 2 H), 7.42–7.37 (m, 3 H), 6.89 (s, 1H).

6b) 5-Phenyl-3-ureido-thiophene-2-sulfonic acid amide

The title compound was prepared from 6a by following the procedure in example 3d. This compound is a white solid: MS (ES) 298 (M+H)$^+$; $^1$H NMR (400 MHz, CD$_3$SOCD$_3$) δ8.30 (s, 1 H), 8.10 (s, 1 H), 7.68–7.39 (m, 8 H), 6.65 (s, 1 H).

This invention provides a pharmaceutical composition, which comprises a compound according to Formula, I and a pharmaceutically acceptable carrier, diluent or excipient. Accordingly, the compounds of Formula I may be used in the manufacture of a medicament. Pharmaceutical compositions of the compounds of Formula I prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The methods of the present invention include topical inhaled and intracolonic administration of the compounds of Formula I. By topical administration is meant non-systemic administration, including the application of a compound of the invention externally to the epidernis, to the buccal cavity and instillation of such a compound into the ear, eye and nose, wherein the compound does not significantly enter the blood stream. By systemic administration is meant oral, intravenous, intraperitoneal and intramuscular administration. The amount of a compound of the invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician While it is possible for an active ingredient to be administered alone as the raw chemical, it is preferable to present it as a pharmaceutical formulation. The active ingredient may comprise, for topical administration, from 0.01 to 5.0 wt % of the formulation.

The topical formulations of the present invention, both for veterinary and for human medical use, comprise an active ingredient together with one or more acceptable carriers therefor and optionally any other therapeutic ingredients. The carrier must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container, which is then sealed and sterilized by autoclaving, or maintaining at 90–100 C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap, a mucilage, an oil of natural origin such as almond, corn, arachis, castor or olive oil, wool fat or its derivatives, or a fatty acid such as stearic or oleic acid together with an alcohol such as propylene glycol or macrogols. The formulation may incorporate any suitable surface active agent such as an anionic, cationic or non-ionic surface active agent such as sorbitan esters or polyoxyethylene derivatives thereof. Suspending agents such as natural gums, cellulose derivatives or in organic materials such as silicaceous silicas, and other ingredients such as lanolin, may also be included.

Utility of the Present Invention

The compounds of Formula I are useful as inhibitors of the IKK-beta kinase phosphorylation of IκB and as such are inhibitors of NF-κB activation. The present method utilizes compositions and formulations of said compounds, including pharmaceutical compositions and formulations of said compounds.

The present invention particularly provides methods of treatment of diseases associated with inappropriate NF-κB activation, which methods comprise administering to an animal, particularly a mammal, most particularly a human in need thereof one or more compounds of Formula I. The present invention particularly provides methods for treating inflammatory and tissue repair disorders, particularly rheumatoid arthritis, inflammatory bowel disease, asthma and COPD (chronic obstructive pulmonary disease) osteoarthritis, osteoporosis and fibrotic diseases; dermatosis, including psoriasis, atopic dermatitis and ultraviolet radiation (UV)-induced skin damage, autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including aquired immune deficiency syndrome (AIDS), adult respiratory distress syndrome and Ataxia Telangiestasia.

For acute therapy, parenteral administration of one or more compounds of Formula I is useful. An intravenous infusion of the compound in 5% dextrose in water or normal saline, or a similar formulation with suitable excipients, is most effective, although an intramuscular bolus injection is also useful. Typically, the parenteral dose will be about 0.01 to about 50 mg/kg; preferably between 0.1 and 20 mg/kg, in a manner to maintain the concentration of drug in the plasma at a concentration effective to inhibit IKK-beta and therefore activation of NF-κB. The compounds are administered one to four times daily at a level to achieve a total daily dose of about 0.4 to about 80 mg/kg/day. The precise amount of a compound used in the present method which is therapeutically effective, and the route by which such compound is best administered, is readily determined by one of ordinary skill in the art by comparing the blood level of the agent to the concentration required to have a therapeutic effect.

The compounds of Formulas I may also be administered orally to the patient, in a manner such that the concentration of drug is sufficient to inhibit IKK-beta and therefore activation of NF-κB or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

The compounds of Formulas I may also be administered topically to the patient, in a manner such that the concentration of drug is sufficient to inhibit IKK-beta and therefore activation of NF-κB or to achieve any other therapeutic indication as disclosed herein. Typically, a pharmaceutical composition containing the compound is administered in a topical formulation of between about 0.01% to about 5% w/w.

No unacceptable toxicological effects are expected when compounds of the present invention are administered in accordance with the present invention.

The ability of the compounds described herein to inhibit the activation of NF-κB is clearly evidenced in their ability to inhibit the phosphorylation of the N-terminal fragment of IκB-α by IKK-β(see Table 1 for examples). These compounds also block the degradation of IκB-α and the nuclear translocation of NF-κB in human monocyctes and other mammalian cells upon activation of the cells with a pro-inflammatory stimulii (e.g., TNF-α, LPS, etc.). In addition these compounds inhibit pro-inflammatory mediator production from LPS-stimulated human monocytes and stimulated human primary synovial fibroblasts. The utility of the present NF-κB inhibitors in the therapy of diseases is premised on the importance of NF-κB activation in a variety of diseases.

NF-κB plays a key role in the regulated expression of a large number of pro-inflammatory mediators including cytokines such as TNF, IL-1β, IL-6 and IL-8 (Mukaida et al., 1990; Liberman and Baltimore, 1990; Matsusaka et al., 1993), cell adhesion molecules, such as ICAM and VCAM (Marui et al., 1993; Kawai et al., 1995; Ledebur and Parks, 1995), and inducible nitric oxide synthase (iNOS) (Xie et al., 1994; Adcock et al., 1994). (Full reference citations are at the end of this section). Such mediators are known to play a role in the recruitment of leukocytes at sites of inflammation and in the case of iNOS, may lead to organ destruction in some inflammatory and autoimmune diseases (McCartney-Francis et al., 1993; Kleemann et al., 1993.

Evidence for an important role of NF-κB in inflammatory disorders is obtained in studies of asthmatic patients. Bronchial biopsies taken from mild atopic asthmatics show significant increases in the number of cells in the submucosa staining for activated NF-κB, total NF-κB, and NF-κB- regulated cytokines such as GM-CSF and TNFα compared to biopsies from normal non-atopic controls (Wilson et al., 1998). Furthermore, the percentage of vessels expressing NF-κB immunoreactivity is increased as is IL-8 immunoreactivity in the epithelium of the biopsy specimens (Wilson et al., 1998). As such, inhibition of IL-8 production through the inhibition of NF-κB, as has been demonstrated by these compounds would be predicted be beneficial in airway inflammation.

Recent studies suggest that NF-κB may also play a critical role in the pathogenesis of inflammatory bowel disease (IBD). Activated NF-κB is seen in colonic biopsy specimens from Chron's disease and ulcerative colitis patients (Ardite et al., 1998; Rogler et al., 1998; Schreiber et al., 1998). Activation is evident in the inflamed mucosa but not in uninflamed mucosa (Ardite et al., 1998; Rogler et al., 1998) and is associated with increased IL-8 mRNA expression in the same sites (Ardite et al., 1998). Furthermore, corticosteroid treatment strongly inhibits intestinal NF-κB activation and reduces colonic inflammation (Ardite et al., 1998; Schreiber et al., 1998). Again, inhibition of IL-8 production through the inhibition of NF-κB, as has been demonstrated by these compounds would be predicted be beneficial in inflammatory bowel disease.

Animal models of gastrointestinal inflammation provide further support for NF-κB as a key regulator of colonic inflammation. Increased NF-κB activity is observed in the lamina propria macrophages in 2,4,6,-trinitrobenzene sulfonic acid (TNBS)-induced colitis in mice with p65 being a major component of the activated complexes (Neurath et al., 1996; Neurath and Pettersson, 1997). Local administration of p65 antisense abrogates the signs of established colitis in the treated animals with no signs of toxicity (Neurath et al., 1996; Neurath and Pettersson, 1997). As such, one would predict that small molecule inhibitors of NF-κB would be useful in the treatment of IBD.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising human rheumatoid synovium (Handel et al., 1995; Marok et al., 1996; Sioud et al., 1998) and in animal models of the disease (Tsao et al., 1997). The staining is associated with type A synoviocytes and vascular endothelium (Marok et al., 1996). Furthermore, constitutive activation of NF-κB is seen in cultured synoviocytes (Roshak et al., 1996; Miyazawa et al., 1998) and in synovial cell cultures stimulated with IL-1β or TNFα (Roshak et al., 1996; Fujisawa et al., 1996; Roshak et al., 1997). Thus, the activation of NF-κB may underlie the increased cytokine production and leukocyte infiltration characteristic of inflamed synovium. The ability of these compounds to inhibit NF-κB and thereby inhibit the production of pro-inflammatory mediators (e.g. cytokines and prostanoids) by these cells would be predicted to yield benefit in rheumatoid arthritis.

Biological Assays:

The compounds of this invention may be tested in one of several biological assays to determine the concentration of compound, which is required to have a given pharmacological effect.

NF-κB activity may also be measured in an electrophoretic mobility shift assay (EMSA) to assess the presence of NF-κB protein in the nucleus. The cells of interest are cultured to a density of $1 \times 10^6$/mL. The cells are harvested by centrifugation, washed in PBS without $Ca^{2+}$ and $Mg^{2+}$ and resuspended in PBS with $Ca^{2+}$ and $Mg^{2+}$ at $1 \times 10^7$ cells/mL. To examine the effect of compound on the activation of NF-κB, the cell suspensions are treated with various concentrations of drug or vehicle (DMSO, 0.1%) for 30 min. at 37° C. prior to stimulation with TNF-α (5.0 ng/mL) for an additional 15 min. Cellular and nuclear extracts are prepared follows. Briefly, at the end of the incubation period the cells ($1 \times 10^7$ cells) are washed 2× in PBS without $Ca^{2+}$ and $Mg^{2+}$. The resulting cell pellets are resuspended in 20 uL of Buffer A (10 mM Hepes (pH 7.9), 10 mM KCl, 1.5 mM $MgCl_2$, 0.5 mM dithiothreitol (DTT) and 0.1% NP-40) and incubated on ice for 10 min. The nuclei are pelleted by microcentrifugation at 3500 rpm for 10 min at 4° C. The resulting supernatant was collected as the cellular extract and the nuclear pellet was resuspended in 15 uL Buffer C (20 mM Hepes (pH 7.9), 0.42 M NaCl, 1.5 mM $MgCl_2$, 25% glycerol, 0.2 mM EDTA, 0.5 mM DTT, and 0.5 mM phenylmethylsulphonyl fluoride (PMSF)). The suspensions are mixed gently for 20 min at 4° C. then microcentrifuged at 14,000 rpm for 10 min at 4° C. The supernatant is collected and diluted to 60 uL with Buffer D (20 mM Hepes (pH 7.9), 50 mM KCl, 20% glycerol, 0.2 mM EDTA, 0.5 mM DTT, and 0.5 mM PMSF). All samples are stored at −80° C. until analyzed. The protein concentration of the extracts is determined according to the method of Bradford (Bradford, 1976) with BioRad reagents.

The effect of compounds on transcription factor activation is assessed in an electrophoretic mobility shift assay (EMSA) using nuclear extracts from treated cells as described above. The double stranded NF-κB consensus oligonucleotides (5'-AGTTGAGGGGACTTTCCCAGGC-3') are labelled with $T_4$ polynucleotide kinase and [g-$^{32}$P] ATP. The binding mixture (25 uL) contains 10 mM Hepes-NaOH (pH 7.9), 4 mM Tris-HCl (pH 7.9), 60 mM KCl, 1 mM EDTA, 1 mM dithiothreitol, 10% glycerol, 0.3 mg/mL bovine serum albumin, and 1 ug poly(dI-dC)•poly(dI-dC). The binding mixtures (10 ug nuclear extract protein) are incubated for 20 min at room temperature with 0.5 ng of $^{32}$P-labelled oligonucleotide (50,000–100,000 cpm) in the presence or absence of unlabeled competitor after which the mixture is loaded on a 4% polyacrylamide gel prepared in 1× Tris borate/EDTA and electrophoresed at 200 V for 2 h. Following electrophoresis the gels are dried and exposed to film for detection of the binding reaction.

The effect of compounds on the phosphorylation of IκB may be monitored in a Western blot. Cellular extracts are subjected to sodium dodecyl sulfate-polyacrylamide gel electrophoresis (SDS-PAGE) on 10% gels (BioRad, Hercules, Calif.) and the proteins transferred to nitrocellulose sheets (Hybond™-ECL, Amersham Corp., Arlington Heights, Ill.). Immunoblot assays are performed using a polyclonal rabbit antibody directed against IκBα or IκBβ followed with a peroxidase-conjugated donkey anti-rabbit secondary antibody (Amersham Corp., Arlington Heights, Ill.). Immunoreactive bands are detected using the Enchanced Cherniluminescence (ECL) assay system (Amersham Corp., Arlington Heights, Ill.).

Assays for IκB kinases were conducted as follows: IKK-α was expressed as a hexa-histidine tagged protein in baculovirus-infected insect cells and purified over a Ni-NTA affinity column. Kinase activity was assayed using 50 ng of purified protein in assay buffer (20 mM Hepes, pH 7.7, 2 mM $MgCl_2$, 1 mM $MnCl_2$, 10 mM β-glycerophosphate, 10 mM NaF, 10 mM PNPP, 0.3 mM $Na_3VO_4$, 1 mM benzamidine, 2 μM PMSF, 10 μg/ml aprotinin, 1 ug/mL leupeptin, 1 ug/mL pepstatin, 1 mM DTT) containing various concentrations of compound or DMSO vehicle and ATP as indicated (Pharmacia Biotech Inc., Piscataway, N.J.). The reaction was started by the addition of 200 ng IκB-GST (Santa Cruz Biotechnology, Inc., Santa Cruz, Calif.), in a total volume of 50 uL. The reaction was allowed to proceed for 1 h. at 30° C. after which the reaction was terminated by the addition of EDTA to a final concentration of 20 mM. Kinase activity was determined by dissociation-enhanced lanthanide fluorescence immunoassay (Wallac Oy, Turku, Finland) using a phospho-IκB-α (Ser32) antibody (New England Biolabs, Inc., Beverly, Mass.) and an $Eu^{3+}$-labelled anti-rabbit IgG (Wallac Oy, Turku, Finland). The plates were read in a VICTOR 1420 Multilabel Counter (Wallac), using a standard europium protocol (excitation 340 nm, emission 615 nm; fluorescence measured for 400 μs after a 400 usec delay). Data are expressed as fluorescence (cps) units.

IKK-β was expressed as a GST-tagged protein, and its activity was assessed in a 96-well scintillation proximity assay (SPA). Briefly, IKK-β was diluted in assay buffer as described above (20 nM final), with various concentrations of compound or DMSO vehicle, 240 nM ATP and 200 nCi [γ-$^{33}$P]-ATP (10 mCi/mL, 2000 Ci/mmol; NEN Life Science Products, Boston, Mass.). The reaction was started with the addition of a biotinylated peptide comprising amino acids 15–46 of IκB-α (American Peptide) to a final concentration of 2.4 μM, in a total volume of 50 uL. The sample incubated for one hour a 30° C., followed by the addition of 150 uL of stop buffer (PBS w/o $Ca^{2+}$, $Mg^{2+}$, 0.1% Triton X-100 (v/v), 10 mM EDTA) containing 0.2 mg streptavidin-coated SPA PVT beads (Amersham Pharmacia Biotech, Piscataway, N.J.). The sample was mixed, incubated for 10 min. at room temperature, centrifuged (1000×g, 2 minutes), and measured on a Hewlett-Packard TopCount.

The effect of IKK-β inhibitors on primary synovial fibroblast mediator production was assesses as follows: Primary cultures of human RSF were obtained by enzymatic digestion of synovium obtained from adult patients with rheumatoid arthritis as previously described (Roshak et al., 1996b). Cells were cultured in Earl's Minimal Essential Medium (EMEM) which contained 10% fetal bovine serum (FBS), 100 units/ml penicillin and 100 μg/ml streptomycin (GIBCO, Grand Island, N.Y.), at 37° C. and 5% $CO_2$. Cultures were used at passages 4 through 9 in order to obtain a more uniform type B fibroblast population. For some studies, fibroblasts were plated at 5×10$^4$ cells/mL in 16 mm (diameter) 24 well plates (Costar, Cambridge, Mass.). Cells (70–80% confluence) were exposed to IL-1β (1 ng/mL) (Genzyme, Cambridge, Mass.) for the designated time. Drugs in DMSO vehicle (1%) were added to the cell cultures 15 minutes prior to the addition of IL-1. Studies were conducted 3–4 times using synovial cells from different donors. RSF cellular extracts were prepared from cells treated as described above. Briefly, human RSF were removed by trypsin/EDTA, washed, and harvested by centrifugation. Cellular extracts were prepared as previously described (Dignam et al., 1983; Osborn, et al., 1989). Briefly, at the end of the incubation period the cells (1×10$^7$ cells) were washed 2× in PBS without $Ca^{2+}$ and $Mg^{2+}$. The resulting cell pellets were resuspended in 20 uL of Buffer A (10 mM Hepes (pH 7.9), 10 mM KCl, 1.5 mM $MgCl_2$, 0.5 mM.

Effect of IKK-β inhibition on human monocyte stimulated eicosanoid and cytokine production was assessed as follows: Monocytes were isolated from heparinized whole blood by double gradient centrifugation as previously described. Isolated monocyte enriched PBMCs were then adhered to 24 well culture plates at 2×10$^6$ cells/mL in RPMI 1640 10% FBS (Hyclone, Logan, Utah) for 2 h. to further enrich the monocyte population. The media was then removed, cells washed once with RPMI 1640, and 1 mL RPMI 1640 10% FBS was added to the wells. Test compounds are added to the wells with a final vehicle concentration of 0.05% DMSO. Monocytes were activated by the addition of 200 ng/mL endotoxin (LPS; *E. coli* serotype 026:B6)(Sigmna, St. Louis, Mo.) and incubated for 24 hrs. Cell-free supernates were analyzed by ELISA for TNF-α (EIA developed at SB), $PGE_2$ (Cayman Chemical, Ann Arbor, Mich.), and IL-8 and IL-6 Biosource International, Camarillo, Calif.). Viability of the cells was determined by trypan blue exclusion.

Effect of IKK-β inhibitors on phorbol ester-induced inflammation was assessed as follows: The inflanmmatory response induced by the cutaneous application of phorbol ester (PMA) to the external pinnae of Balb/c mice has proven to be a useful model to examine multifactorial inflammatory cell infiltration and inflammatory alteration of epidermis. The intense inflammatory lesion is dominated by neutrophil infiltration, which can be easily quantified by measurement tissue concentration myeloperoxidase, an azuriphilic granular enzyme present in neutrophils. In addition, the overall intensity of the inflammatory response can be measured by determination of ear thickness. Balb/c mice (n=6/group) were administered drug treatment or vehicle followed by PMA (4 ug/ear). The mice were sacrificed 4 h. later, the ear thickness determined and NF-κB activation was monitored by IκBα western or EMSA analysis.

Effect of IKK-β inhibitors on rat carrageenan-induced paw edema was assessed as follows: Male Lewis rats (Charles River-Raleigh, N.C.) were housed and allowed free access to food and water, and weighed between 200–275 g for each experiment. Compound or vehicle (0.5% Tragacanth (p.o.) or 10% DMSO, 5% DMA, 30% Cremophor (i.p.)) was administered 30 minutes to 1 hour prior to the carrageenan injection. Edema was induced by injection of 1% carrageenan in sterile dH2O (0.05 ml/paw) into the plantar surface of the right hindpaw. Paw thickness was measured prior to administration of compound or vehicle, and again at 3 hours, to determine change in paw volume. Rats were euthanized by CO2 inhalation and the right hindfoot was removed, immediately frozen in liquid nitrogen and stored at −80 C. for analysis.

All publications, including, but not limited to, patents and patent applications cited in this specification, are herein incorporated by reference as if each individual publication were specifically and individually indicated to be incorporated by reference herein as though fully set forth.

The above description fully discloses how to make and use the present invention. However, this invention is not limited to the particular embodiments described hereinabove, but includes all modification thereof within the scope of the appended claims and their equivalents. Those skilled in the art will recognize through routine experimentation that various changes and modifications can be made without departing from the scope of this invention.

We claim:

1. A compound according to formula (I) hereinbelow:
(I) herein below:

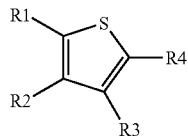

$R_1$ is $CONH_2$, or $SO_2NH_2$;
$R_2$ is $NR_5R_6$;
$R_3$ is H, or halogen;
$R_4$ is aryl, or heteroaryl;
$R_5$ is H, or alkyl;
$R_6$ is selected from the group consisting of CO-alkyl, $SO_2$-alkyl, $CONH_2$, CONH-alkyl, CONH-aryl, CONH-heteroaryl, $CSNH_2$, CSNH-alkyl, CSNH-aryl, CSNH-heteroaryl, $SO_2NH_2$, $SO_2NH$-alkyl, $SO_2NH$-aryl, and $SO_2NH$-heteroaryl;
and pharmaceutically acceptable salts, hydrates and solvated thereof;
provided that when $R_1$ is $CONH_2$, $R_2$ is not $NHCONH_2$.

2. A compound according to claim 1 wherein the compound is selected from the group consisting of:
   3-Amino-5-phenyl-thiophene-2-carboxylic acid amide;
   3-Amino-5-(4-methoxy-phenyl)-thiophene-2-carboxylic acid amide;
   3-Amino-5-(4-isobutyl-phenyl)-thiophene-2-carboxylic acid amide;
   4-Amino-[2,3']bithiophenyl-5-carboxylic acid amide;
   3-Amino-5-(4-fluoro-phenyl)-thiophene-2-carboxylic acid amide;
   3-Amino-5-(4-chloro-phenyl)-thiophene-2-carboxylic acid amide;
   4-Amino-[2,2']bithiophenyl-5-carboxylic acid amide;
   3-Acetylamino-5-(4-chloro-phenyl)-thiophene-2-carboxylic acid amide; and
   3-Acetylamino-5-(4-fluoro-phenyl)-thiophene-2-carboxylic acid amide.

3. A compound according to claim 2 wherein the compound is selected from:
   3-Acetylamino-5-(4-chloro-phenyl)-thiophene-2-carboxylic acid amide; and
   3-Acetylamino-5-(4-fluoro-phenyl)-thiophene-2-carboxylic acid amide.

4. A method of treating a disease characterized by pathological NF-κB activation comprising inhibiting the pathological activation by administering to a patient in need thereof an effective amount of a compound according to claim 1.

5. A method according to claim 4 wherein the disease is an inflammatory or tissue repair disorder.

6. A method according to claim 5 wherein the disease is selected from the group consisting of particularly rheumatoid arthritis, inflammatory bowel disease, asthma and COPD (chronic obstructive pulmonary disease) osteoarthritis, osteoporosis and fibrotic diseases, dermatosis, including psoriasis, atopic dermatitis and ultraviolet radiation (UV)-induced skin damage, autoimmune diseases including systemic lupus eythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including aquired immune deficiency syndrome (AIDS), adult respiratory distress syndrome, and Ataxia Telangiestasia.

7. A method according to claim 4 wherein said disease is dermatosis.

8. A method according to claim 4 wherein the disease is selected from the group consisting of: psoriasis, atopic dermatitis, and UV-induced skin damage.

9. A method according to claim 4 wherein he disease is selected from the group consisting of autoimmune diseases; tissue and organ rejection, Alzheimer's disease, stroke, atherosclerosis, restenosis, diabetes, glomerulonephritis, osteoarthritis, osteoporosis, and Ataxia Telangiestasia.

10. A method according to claim 4 wherein said disease is an autoimmune disease.

11. A method according to claim 10 wherein the autoimmune disease is systemic lupus eythematosus, multiple sclerosis, psoriatic arthritis alkylosing spondylitis or diabetes.

12. A method according to claim 1 wherein the disease is cancer or cachexia.

13. A method according to claim 12 wherein the cancer is Hodgkins disease.

14. A method according to claim 4 wherein the disease is inflammation associated with infection.

15. A method according to claim 4 wherein the disease is AIDS.

16. A method according to claim 4 wherein the disease is adult respiratory distress syndrome.

17. A method according to claim 4 wherein said compounds inhibit NF-κB and checkpoint kinase.

\* \* \* \* \*